United States Patent [19]

Hattler

[11] Patent Number: 5,376,069

[45] Date of Patent: * Dec. 27, 1994

[54] INFLATABLE PERCUTANEOUS OXYGENATOR WITH INTERNAL SUPPORT

[76] Inventor: Brack G. Hattler, 5226 Westminster Pl., Pittsburgh, Pa. 15232

[*] Notice: The portion of the term of this patent subsequent to Jun. 16, 2009 has been disclaimed.

[21] Appl. No.: 56,127

[22] Filed: Apr. 30, 1993

Related U.S. Application Data

[63] Continuation-in-part of Ser. No. 878,724, May 5, 1992, Pat. No. 5,219,326, which is a continuation-in-part of Ser. No. 676,262, Mar. 27, 1991, Pat. No. 5,122,113.

[51] Int. Cl.$^5$ .............................................. A61M 37/00
[52] U.S. Cl. ...................................... 604/26; 604/49; 604/96; 128/DIG. 3; 623/3
[58] Field of Search ............................. 128/DIG. 3; 261/DIG. 28; 604/23–28, 49, 43, 96, 99, 101; 606/192, 194–196; 423/1, 3, 9, 11, 12

[56] References Cited

U.S. PATENT DOCUMENTS

| | | | |
|---|---|---|---|
| 3,505,686 | 4/1970 | Bodell | 3/1 |
| 4,138,288 | 2/1979 | Lewin | 128/DIG. 3 |
| 4,159,720 | 7/1979 | Burton | 128/260 |
| 4,346,006 | 8/1982 | Kopp et al. | 210/321.4 |
| 4,576,590 | 3/1986 | Fiddian-Green | 604/26 |
| 4,583,969 | 4/1986 | Mortensen | 604/49 |
| 4,631,053 | 12/1986 | Taheri | 604/49 |
| 4,743,250 | 5/1988 | Kitagawa et al. | 623/1 |
| 4,791,054 | 12/1988 | Hamada et al. | 128/DIG. 3 |
| 4,793,350 | 12/1988 | Mar et al. | 128/344 |
| 4,821,722 | 4/1989 | Miller et al. | 128/344 |
| 4,850,958 | 7/1989 | Berry et al. | 604/26 |
| 4,911,689 | 3/1990 | Hattler | 604/26 |
| 4,950,224 | 8/1990 | Gorsuch et al. | 604/26 |
| 4,986,809 | 1/1991 | Hattler | 604/26 |
| 5,037,383 | 8/1991 | Vaslef et al. | 604/26 |
| 5,122,113 | 6/1992 | Hattler | 604/26 |

OTHER PUBLICATIONS

Tanishita et al., "Augmentation of Gas Transfer With Pulsatile Flow in the Coiled Tube Member Oxygenator Design", 26 Trans. Am. Soc. Artif. Intern. Organs 561 (1980).

Wampler et al., "An Axial Flow Ventricular Assist Device With Integrated Motor Drive" (Publ. date unknown).

Butler et al., "Development of an Implantable Flow LVAS" (Publ. date uknown).

Jegaden et al., "Temporary left ventricular assistance with a Hemopump assist device during acute myocardial infarction" (Letter to the Editor), Journal of Thoracic and Cardiovascular Surgery, Aug. 1990.

Shiiya et al., "Effects of Hemopump Support on Left Ventricular Unloading and Coronary Blood Flow," 37 Trans. Am. Soc. Artif. Intern. Organs (1991).

Berry, "Apparatus and Methods for Furling and Introducing An Extrapulmonary Blood Gas Exchange Device" (International Application Published Under the Patent Cooperation Treaty), International Publication No. WO 91/09642, Published Jul. 11, 1991.

Primary Examiner—C. Fred Rosenbaum
Assistant Examiner—Michael Rafa
Attorney, Agent, or Firm—Gary M. Polumbus

[57] ABSTRACT

An inflatable percutaneous oxygenator has an inflatable balloon suitable for insertion into a blood vessel. Oxygen is circulated through a number of gas-permeable passageways (such as hollow gas-permeable fibers) adjacent to the balloon surface to permit diffusion of oxygen and carbon dioxide between the blood vessel and the passageways. Pulsatile flow can be used to increase the rate of cross-diffusion of gases. A pump is used to alternately expand and contract the balloon. This causes movement of the passageways within the blood vessel to minimize streaming or channeling of the blood flow around the oxygenator, maximizes turbulence in the bloodstream, and therefore maximizes diffusion of gases. In one alternative embodiment, the balloon is made of a gas-permeable material and is inflated with oxygen to supplement cross-diffusion of gases with the bloodstream. An external connector with lumens supplies a flow of oxygen to the passageways, exhausts gas from the passageways, and allows inflation and deflation of the balloon by the pump. In one alternative embodiment the balloon has a number of chambers separated by constrictions that restrict the flow of gases between the chambers. This results in a relative phase shift in the inflation and deflation of the balloon chambers to provide peristaltic motion to the balloon.

9 Claims, 11 Drawing Sheets

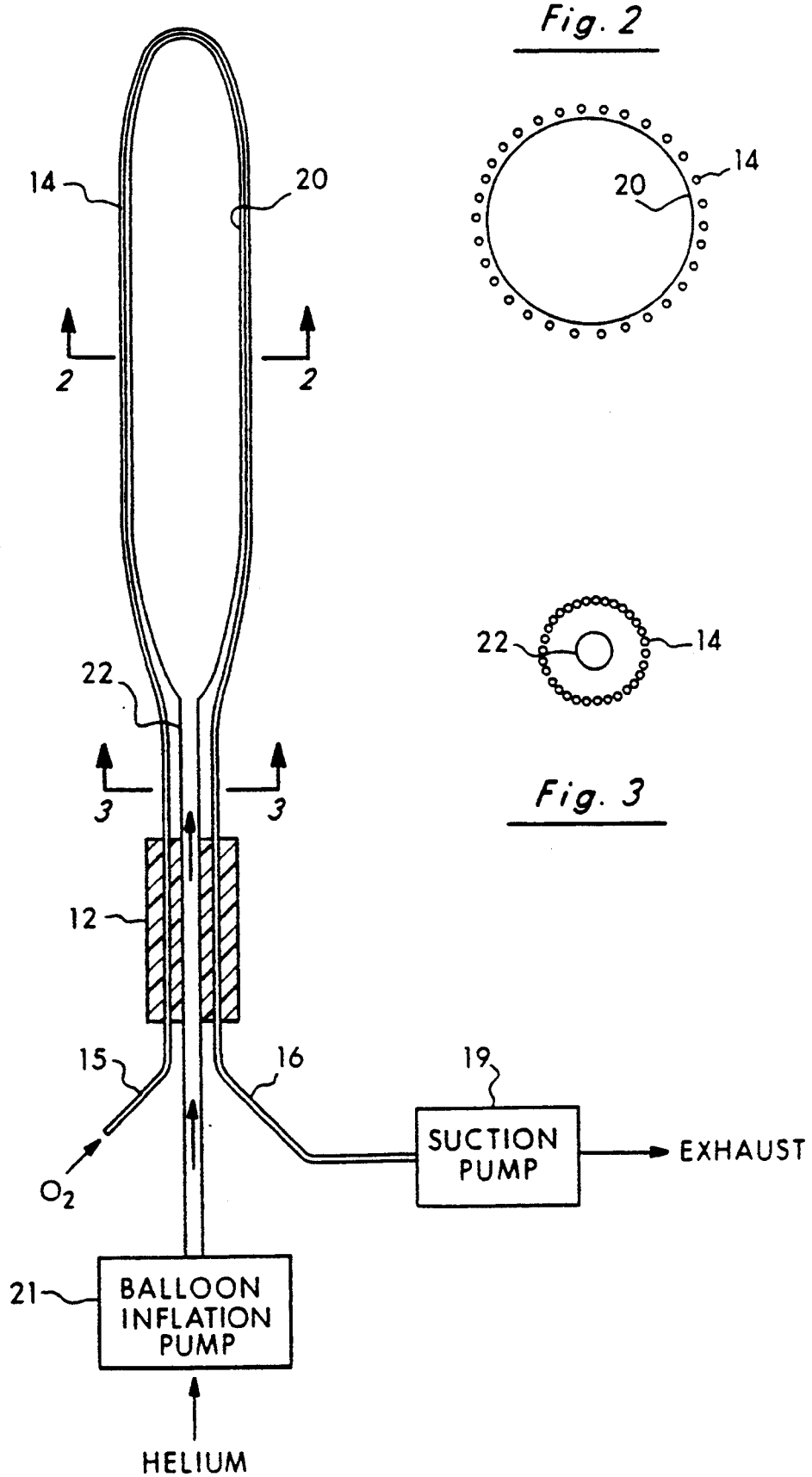

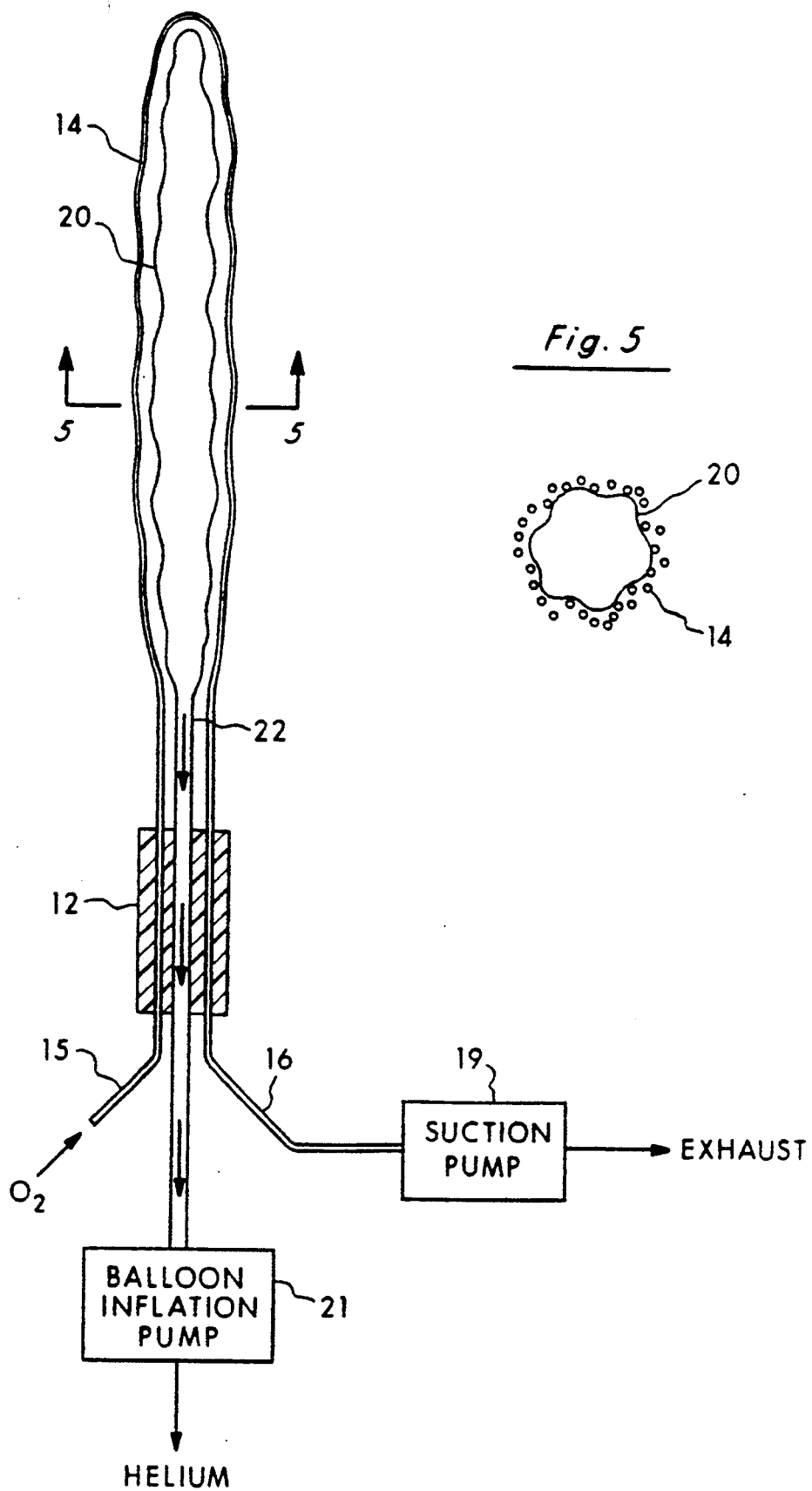

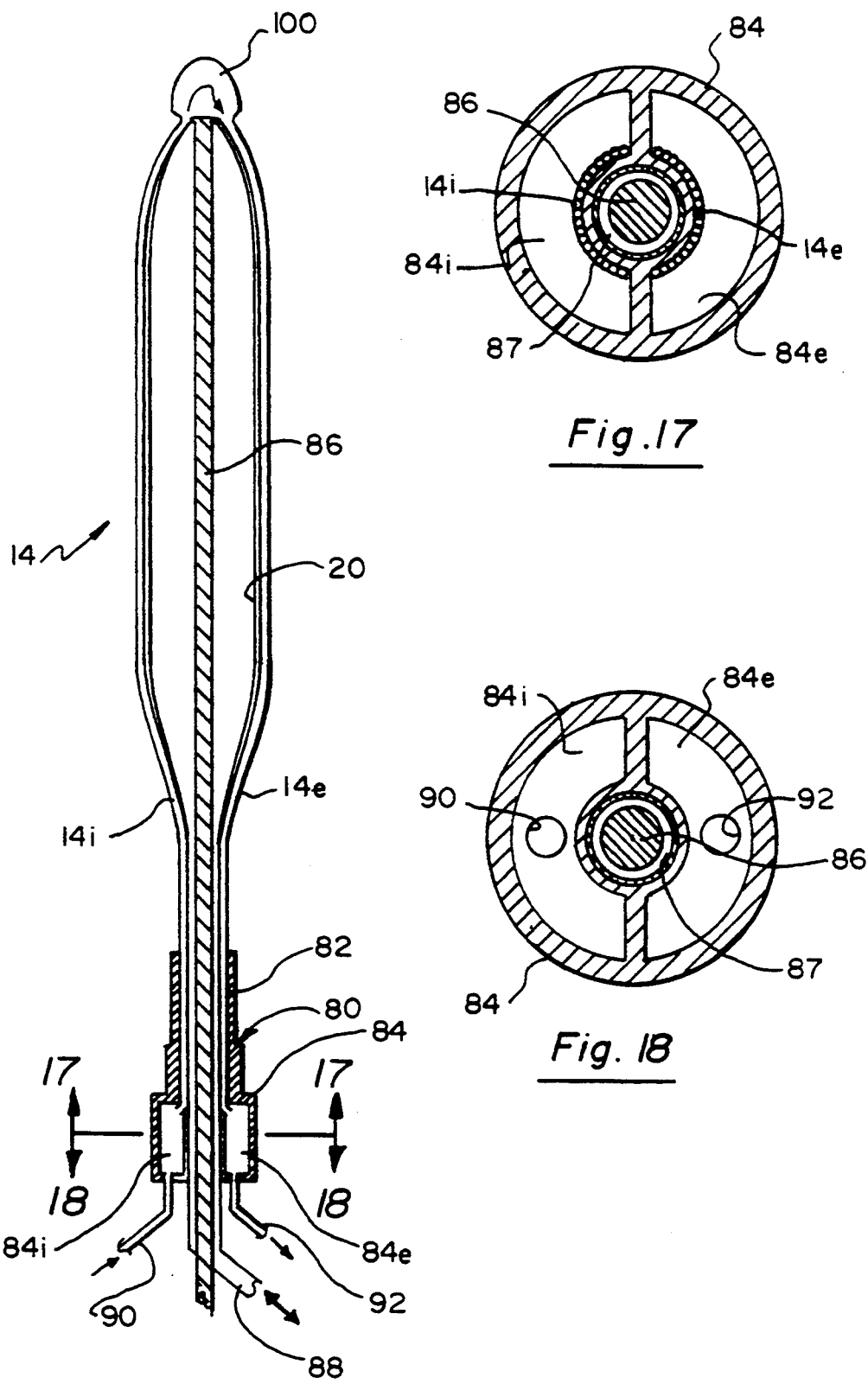

INFLATABLE PERCUTANEOUS OXYGENATOR WITH INTERNAL SUPPORT

RELATED APPLICATIONS

This application is a continuation-in-part of applicant's co-pending U.S. Pat. application Ser. No. 07/878,724 filed May 5, 1992 entitled "Inflatable Percutaneous Oxygenator" U.S. Pat. 5,219,326 which is a continuation-in-part of Ser. No. 676,262, filed Mar. 27, 1991 U.S. Pat. No. 5,122,113 which is of common ownership with the present application.

BACKGROUND OF THE INVENTION

1. Field of the Invention

The present invention relates generally to the field of oxygenators used to increase the oxygen level in a patient's blood. More particularly, the present invention involves a percutaneous oxygenator that can be positioned within a patient's body (e.g. in the inferior vena cava, superior vena cava, the right atrium of the heart, or any combination thereof) and then repeatedly inflated and deflated to minimize streaming of the blood flow around the oxygenator, and thereby maximize the cross-diffusion of oxygen and carbon dioxide.

2. Statement of the Problem

Many types of blood oxygenators are well known in the art. For example, during open heart surgery, the patient is interconnected with an external oxygenator, commonly known as a heart-lung machine, which introduces oxygen into the blood system. Most types of oxygenators use a gas-permeable membrane. Blood flows along one side of the membrane, and oxygen is supplied to the other side of the membrane. Given a sufficient pressure gradient between the oxygen supply and the blood, the oxygen will diffuse through the membrane and into the blood. In addition, carbon dioxide will tend to diffuse from the blood through the membrane.

In other situations, a smaller, implantable oxygenator may be sufficient to adequately supplement the patient's cardiopulmonary function by marginally increasing the oxygen content of the patient's blood. For example, patients suffering from emphysema, pneumonia, congestive heart failure, or other chronic lung disease often have blood oxygen partial pressures of approximately 40 tort. A relatively small increase of 10% to 20% is generally sufficient to adequately maintain the patient. This is a particularly desirable alternative in that it avoids the need to intubate the patient in such cases. In addition, temporary use of this type of oxygenator is sufficient in many cases to tide the patient over an acute respiratory insult. Placing such patients on a conventional respirator is often the beginning of a progressive downhill spiral by damaging the patient's pulmonary tree and thereby causing greater dependence on the respirator.

The effective rate of diffusion in percutaneous oxygenators can be limited in some instances by the problem of "streaming" or "channeling," in which the bloodstream establishes relatively stable patterns of flow around and through the oxygenator. Portions of the oxygenator are exposed to a relatively high velocity, turbulent flow of blood. These conditions tend to increase cross-diffusion of oxygen and carbon dioxide. However, other portions of the oxygenator are exposed to a low velocity, laminar flow of blood which reduces diffusion of gases. Those portions of the oxygenator immediately adjacent to the regions of high blood flow may continue to experience high rates of diffusion, but the remaining portions of the oxygenator tend to have relatively low diffusion rates. Thus, the overall diffusion rate of the oxygenator can be substantially diminished by streaming.

A number of devices and processes have been invented in the past relating to different types of oxygenators and balloon dilatation catheters, including the following:

| Inventor | Patent No. | Issue Date |
| --- | --- | --- |
| Bodell | 3,505,686 | 04/14/70 |
| Burton | 4,159,720 | 07/03/79 |
| Kopp, et al. | 4,346,006 | 08/24/82 |
| Fiddian-Green | 4,576,590 | 03/18/86 |
| Mortensen | 4,583,969 | 04/22/86 |
| Taheri | 6,631,053 | 12/23/86 |
| Kitagawa, et al. | 4,743,250 | 05/10/88 |
| Mar, et al. | 4,793,350 | 12/27/88 |
| Miller, et al. | 4,821,722 | 04/18/89 |
| Berry, et al. | 4,850,958 | 07/25/89 |
| Hattler | 4,911,689 | 03/27/90 |
| Hattler, et al. | 4,986,809 | 01/22/91 |
| Vaslef, et al. | 5,037,383 | 08/06/91 |
| Tanishita, et al., "Augmentation of Gas Transfer with Pulsatile Flow in the Coiled Tube Member Oxygenator Design," 26 Trans. Am. Soc. Artif. Intern. Organs 561 (1980). | | |

Bodell demonstrates the general concept of using gas-permeable fibers to boost the oxygen level of blood. FIGS. 6 and 10 show two variations of this device intended for use inside the body of the patient. In the implantable embodiment of the Bodell device, a tubular casing serves as a shunt either from the pulmonary artery to the left atrium of the heart (FIG. 6), or more generally between an artery and a vein (FIG. 10). A multitude of parallel-connected capillary tubes are used to oxygenate and/or purify the blood circulating through the casing.

FIGS. 3-5 of the Mortensen patent show a transvenous oxygenator made of a plurality of small diameter gas-permeable tubes 32 connected to headers 34 and 36 at each end. However, the specific device disclosed by Mortensen has a significant disadvantage in that two incisions are required. The insertion process is also rather complex. Mortensen is of interest in recognizing a problem with percutaneous oxygenators of laminar flow of blood past the oxygenator which decreases the efficiency of the oxygenator. Mortensen solves the problem by holding the tubes in an undulating pattern with a stylet that runs parallel to the tubes and has been bent into the desired undulating pattern.

Taheri discloses a transvenous oxygenator having a single membrane 16 through which oxygen diffuses. The membrane is disposed within a sheath 18 and both are supported by a flexible wire 20.

Berry, et al., disclose an in vivo extrapulmonary blood gas exchange device having a bundle of elongated gas permeable tubes 12 bound at each end and enclosed within a respective air-tight proximal and distal chambers 28 and 30. A dual lumen tube is situated relative to the gas-permeable tubes such that an outer lumen terminates within the proximal chamber 28 and an inner lumen terminates within the distal chamber 30.

The Hattler patents disclose several embodiments of percutaneous oxygenators. In the simplest embodiment ('689), oxygen is circulated through a plurality of hollow, gas-permeable fibers forming loops inserted through a single incision into a blood vessel. In other embodiments ('809), the fiber loops are bisected and placed in fluid communication with a mixing chamber within a tip at the distal end of the device.

Tanishita, et al., disclose an extracorporeal oxygenator (FIGS. 1A and 1B) in which diffusion of gases was enhanced by application of pulsatile flow superimposed on a steady mean flow. Flow pulsation is introduced in the oxygenator chamber by directly vibrating its bottom plate.

Mar, et al., disclose a liquid filled dilatation catheter having an inflatable balloon. The catheter includes a self-venting passage 43 for venting the balloon to ambient.

Vaslef, et al., disclose an intravascular oxygenator using a plurality of flexible, hollow, gas-permeable fibers.

Miller, et al., disclose a self-venting balloon dilatation catheter. The balloon 56 is provided with a plurality of gas passageways 67 about its exterior surface to permit air to escape from the interior of the balloon but inhibit the passage of the inflation medium from the balloon.

The remaining references disclose various other types of oxygenators of lesser relevance.

Solution to the Problem

The problem of streaming or laminar blood flow, while having been recognized in the Mortensen patent, has not to date been satisfactorily resolved. None of the prior art references known to applicant show a percutaneous oxygenator that can be inflated and deflated to minimize streaming, and thereby maximize cross-diffusion of gases between the patient's bloodstream and the oxygenator.

SUMMARY OF THE INVENTION

This invention provides a percutaneous oxygenator having an inflatable balloon suitable for insertion into a blood vessel. Oxygen is circulated through a number of gas-permeable passageways (such as hollow gas-permeable fibers) adjacent to the balloon surface to permit diffusion of oxygen and carbon dioxide between the blood vessel and the passageways. Pulsatile flow can be used to increase the rate of cross-diffusion of gases. A pump is used to alternately expand and contract the balloon. This causes movement of the passageways within the blood vessel to minimize streaming or channeling of the blood flow around the oxygenator, maximizes turbulence in the bloodstream, and therefore maximizes diffusion of gases. In one alternative embodiment, the balloon is made of a gas-permeable material and is inflated with oxygen to supplement cross-diffusion of gases within the bloodstream. An external connector with lumens supplies a flow of oxygen to the passageways, exhausts gas from the passageways, and allows inflation and deflation of the balloon by the pump. In one alternative embodiment the balloon has a number of chambers separated by constrictions that restrict the flow of gases between the chambers. This results in a relative phase shift in the inflation and deflation of the balloon chambers to provide peristaltic motion to the balloon.

A primary object of the present invention is to provide an oxygenator that minimizes the problem of streaming or channeling that has heretofore limited the effective rate of diffusion of gases in oxygenators.

Another object of the present invention is the provide an oxygenator that can be easily implanted into a patient through a single incision to effectively boost the oxygen level and to remove carbon dioxide from the patient's blood.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 1 is a side cross-sectional view of one embodiment of the present invention with the balloon inflated.

FIG. 2 is another cross-sectional view taken along plane 2—2 of FIG. 1.

FIG. 3 is yet another cross-sectional view taken along plane 3—3 of FIG. 1.

FIG. 4 is a side cross-sectional view corresponding to FIG. 1 in which the balloon has been deflated.

FIG. 5 is another cross-sectional view taken along plane 5—5 of FIG. 4.

FIG. 16 is a cross-sectional view of still another embodiment wherein a solid tube is utilized to support the balloon and fibers.

FIG. 17 is an enlarged section taken along line 17—17 of FIG. 16.

FIG. 18 is an enlarged section taken along line 18—18 of FIG. 16.

DETAILED DESCRIPTION OF THE INVENTION

Figure 6:
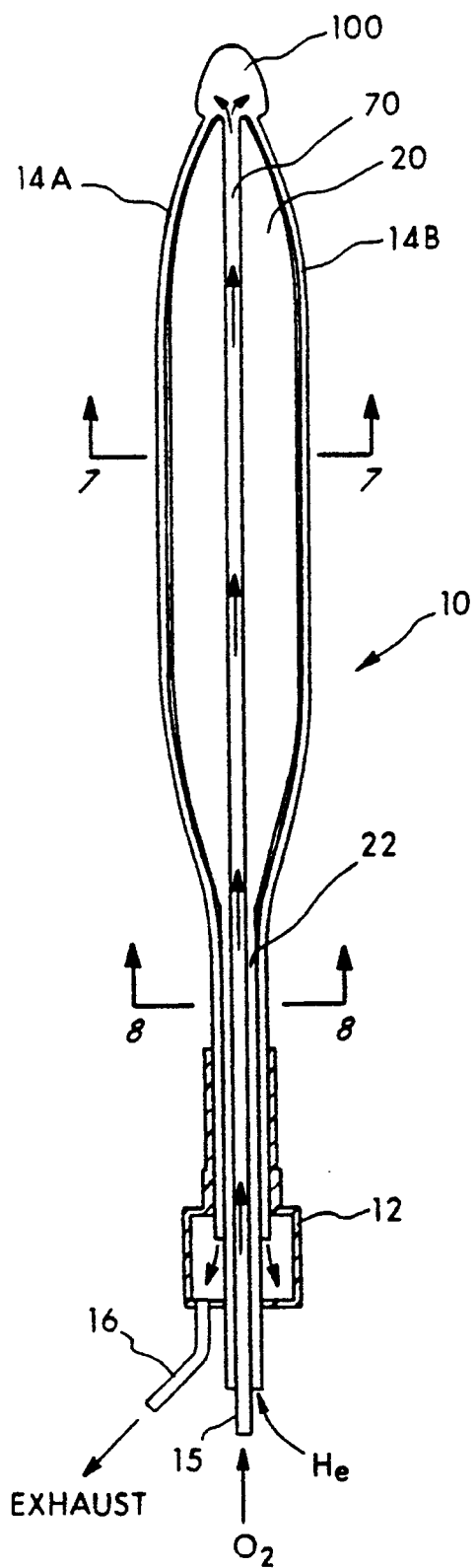
FIG. 6 is a side cross-sectional view of an alternative embodiment of the present invention having a central oxygen supply tube and a hollow tip member.

Turning to FIG. 1, a side cross-sectional view of the oxygenator 10 is shown. The major components are an inflatable balloon 20 and a number of gas passageways 14 which substantially surround the balloon 20. In the preferred embodiment, these gas passageways are a multitude of hollow gas-permeable but liquid impermeable fibers or tubules. The fibers 14 are formed into loops, as shown in FIGS. 1-3, that substantially surround and cover the exterior surface of balloon 20. The gas-permeable walls of the fibers 14 provide a large total surface area for diffusion of oxygen into the bloodstream, and diffusion of carbon dioxide out of the bloodstream. Any of a variety of flexible, hollow, gas-permeable fibers currently available on the market, such as Mitsubishi KPF190M polypropylene fibers, are suitable for this purpose. One embodiment employs fibers having an outside diameter of approximately 262 microns and an inside diameter of approximately 209 microns. To provide a true ideal membrane, the polypropylene fibers should be coated with silicone rubber and bonded with a non-thrombogenic component. Alternatively, multilayered composite hollow fiber membranes can be used for this purpose, such as Mitsubishi MHF200L fibers. These fibers have a composite structure with an outer layer of microporous polyethylene, an intermediate layer of polyurethane which acts as a true membrane, and an inner layer of microporous polyethylene.

The balloon 20 and fiber loops 14 of the device are implanted in the venous system of the patient through a single small incision. For example, the device 10 can be implanted through the right interior jugular vein into the superior vena cava of a patient. For maximum effectiveness, the balloon 20 and fiber loops 14 are fully inserted through the incision up to the level of the connector 12. Insertion of the balloon 20 and fiber loops 14 can be aided by using a conventional introducer similar to the type presently employed to insert a cardiac pacemaker.

The connector 12 provides separate lumens to supply and exhaust the fiber loops 14 and for inflation of the balloon 20. An external pump 21 is connected to the balloon inflation lumen 22 of the connector 12 and can be used to repeatedly inflate and deflate the balloon 20 at a predetermined frequency. A frequency of approximately forty cycles per minute has been experimentally demonstrated to provide satisfactory results in minimizing streaming and maintaining a turbulent flow of blood adjacent to the oxygenator. Any gas or fluid can be pumped into and released from the balloon for this purpose. Helium offers the advantages of having very low viscosity and density for ease of pumping. Carbon dioxide as an inflation gas offers safety features and is quickly dissolved in the bloodstream in the event of balloon leakage. In the preferred embodiment, at least a portion of the fiber loops 14 are secured to the exterior surface of the inflation balloon 20 (e.g. by adhesive bonding). This helps to insure that expansion and contraction of the balloon 20 causes movement of the fibers 14 within the blood vessel. FIGS. 1 and 2 provide cross-sectional views of the oxygenator 10 with the balloon 20 fully inflated. In comparison, FIGS. 4 and 5 show the same oxygenator with the balloon 20 deflated.

After the device has been implanted, a supply of oxygen-containing gas is connected to the second lumen 15 of the connector 12. The oxygen flows through second lumen 15 into the fiber loops 14. Oxygen flows along the interior passageways of the fibers 14 and diffuses outwardly through the gas-permeable walls of the fibers into the surrounding bloodstream. Carbon dioxide also diffuses inwardly from the bloodstream through these gas-permeable walls into the interior of the fibers. Carbon dioxide and any remaining oxygen in the fibers are vented to the atmosphere at the distal ends of the fibers through a third lumen 16 in the connector 12. Negative pressurization can be applied by means of a suction pump 19 connected to the third lumen 16 to enhance gas flow through the fiber loops, and to reduce any risk of gas bubbles escaping from the fibers into the bloodstream. For example, in one embodiment, oxygen is supplied into the fiber loops 14 at a flow rate of approximately 1 to 3 liters per minute and a nominal pressure of approximately 6 to 15 mm Hg. A suction pressure of approximately $-150$ to $-250$ mm Hg is applied by the suction pump 19.

It should be noted that the present invention can also be used to administer anesthetic gases or other medications directly into the patient's blood system. For this purpose, a mixture of oxygen and anesthetic gases flow through the fiber loops of the device and diffuse into the patient's bloodstream.

Figure 7:
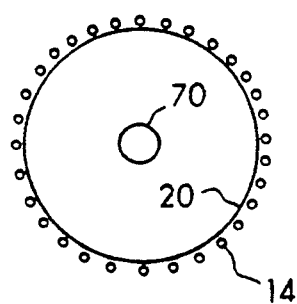
FIG. 7 is another cross-sectional view taken along plane 7—7 of FIG. 6.
Figure 8:
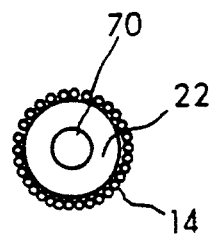
FIG. 8 is another cross-sectional view taken along plane 8—8 of FIG. 6.

FIGS. 6, 7, and 8 show an alternative embodiment of the oxygenator in which a hollow tip member 100 has been added at the distal end of the balloon 20. A central oxygen supply tube 70 extends through the connector 12 and the balloon 20 to the interior of the tip member 100. Each of the fiber loops is bisected at its distal point into two arms 14a and 14b. The resulting ends of the fibers are sealed in fluid communication with the internal cavity of the tip 100. The tip member 100 can be molded from plastic or rubber around the ends of the fibers to prevent the escape of gases at the junction between the fiber ends and the tip member 100. The tip can also be shaped with a tapered contour to ease insertion of the device through an incision. Thus, in this embodiment, oxygen-containing gases flow from an external supply through the oxygen supply tube 70, into the internal cavity of the tip member 100, through both arms 14a and 14b of the fibers, and are then exhausted through the exhaust lumen 16 in the connector 12, as previously described. It should be noted that the oxygen supply tube 70 and the balloon inflation lumen 22 can be formed as concentric tubes as shown in FIGS. 6 and 8. A cross-sectional view of the upper portion of the balloon 20 and the oxygen supply tube 70 is provided in FIG. 7. The oxygen supply tube 70 also acts as a structural support for the tip member 100 and fiber loops 14, and provides a degree of rigidity to aid initial insertion of the device into the blood vessel. Operating parameters would be the same as for the embodiment shown in FIGS. 1-5.

Figure 9:
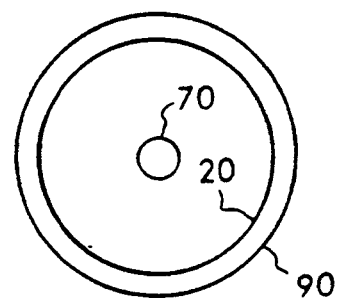
FIG. 9 is a cross-sectional view of an alternative embodiment in which the hollow fibers surrounding the inflation balloon are replaced with a single gas-permeable membrane.

FIG. 9 discloses another alternative embodiment in which the fibers 14 have been replaced by a single gas-permeable membrane 90 surrounding the inflation balloon 20. The resulting structure is essentially a balloon within a balloon. As before, oxygen-containing gas is supplied through the oxygen supply tube 70 to the tip member 100. The oxygen then flows from the tip member 100 back toward the connector 12 through the annular space between the inflation balloon 20 and the outer gas-permeable membrane 90. Cross-diffusion of oxygen and carbon dioxide occurs across the gas-permeable membrane between the annular space and the patient's bloodstream, as previously discussed. Repeated inflation and deflation of the inflation balloon 20 causes corresponding movements in the gas-permeable membrane 90 to minimize streaming. In yet another alternative embodiment, the gas-permeable membrane 90 can be tacked to the exterior surface of the inflation balloon 20 along a number of longitudinal lines to define a plurality of gas passageways extending from the tip member 100 to the connector 12.

Figure 10:
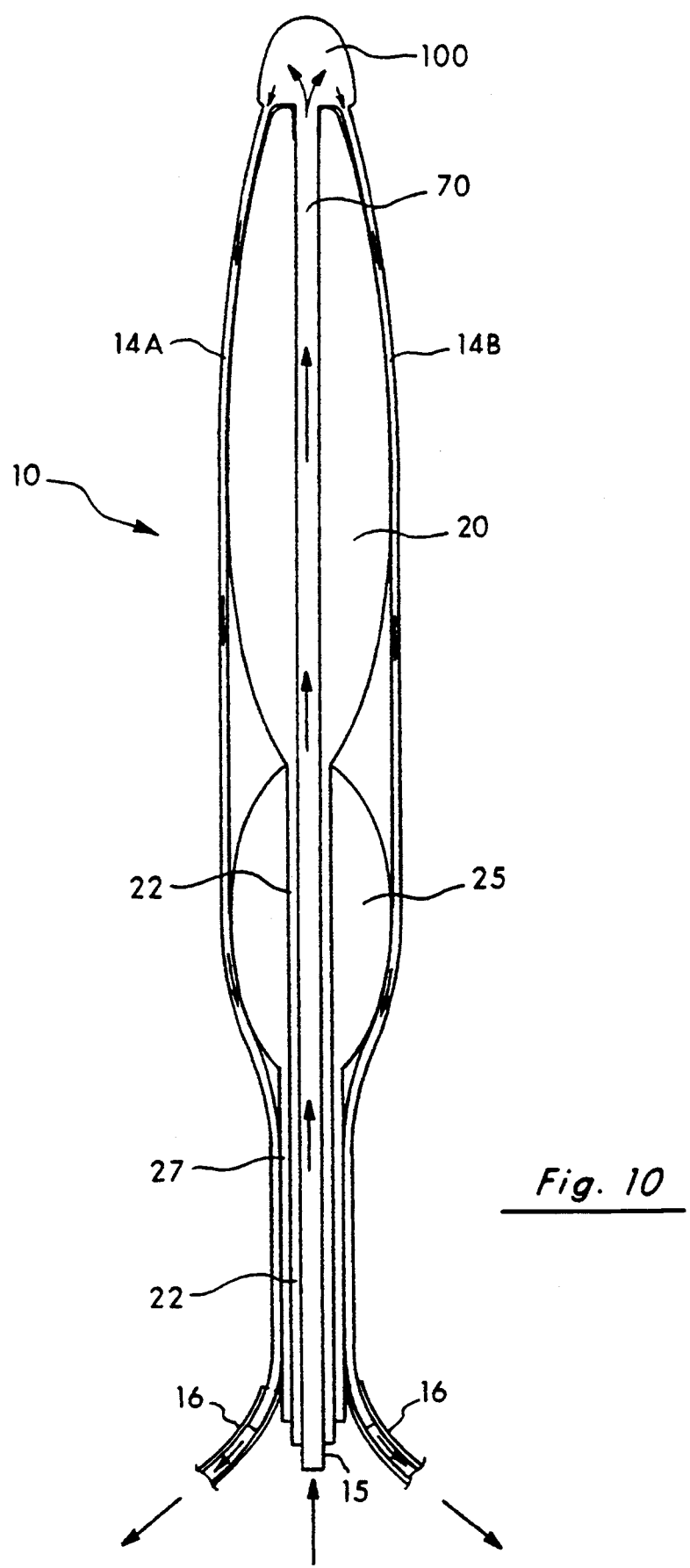
FIG. 10 is a cross-sectional view of another alternative embodiment in which two balloons are inflated and deflated asynchronously.

FIG. 10 shows yet another alternative embodiment of the present invention in which a second inflation balloon 25 has been added adjacent to the first inflation balloon 20. This second balloon 25 has a separate lumen 27 extending through the connector 12 to permit separate inflation and deflation of the second balloon 25 independent of the first balloon 20. In this embodiment, the balloons 20 and 25 will typically be inflated asynchronously (i.e., out of phase with one another) so that resulting turbulence in the patient's bloodstream is maximized. Operating parameters would be the same as for the embodiment shown in FIGS. 1–5.

Figure 11:
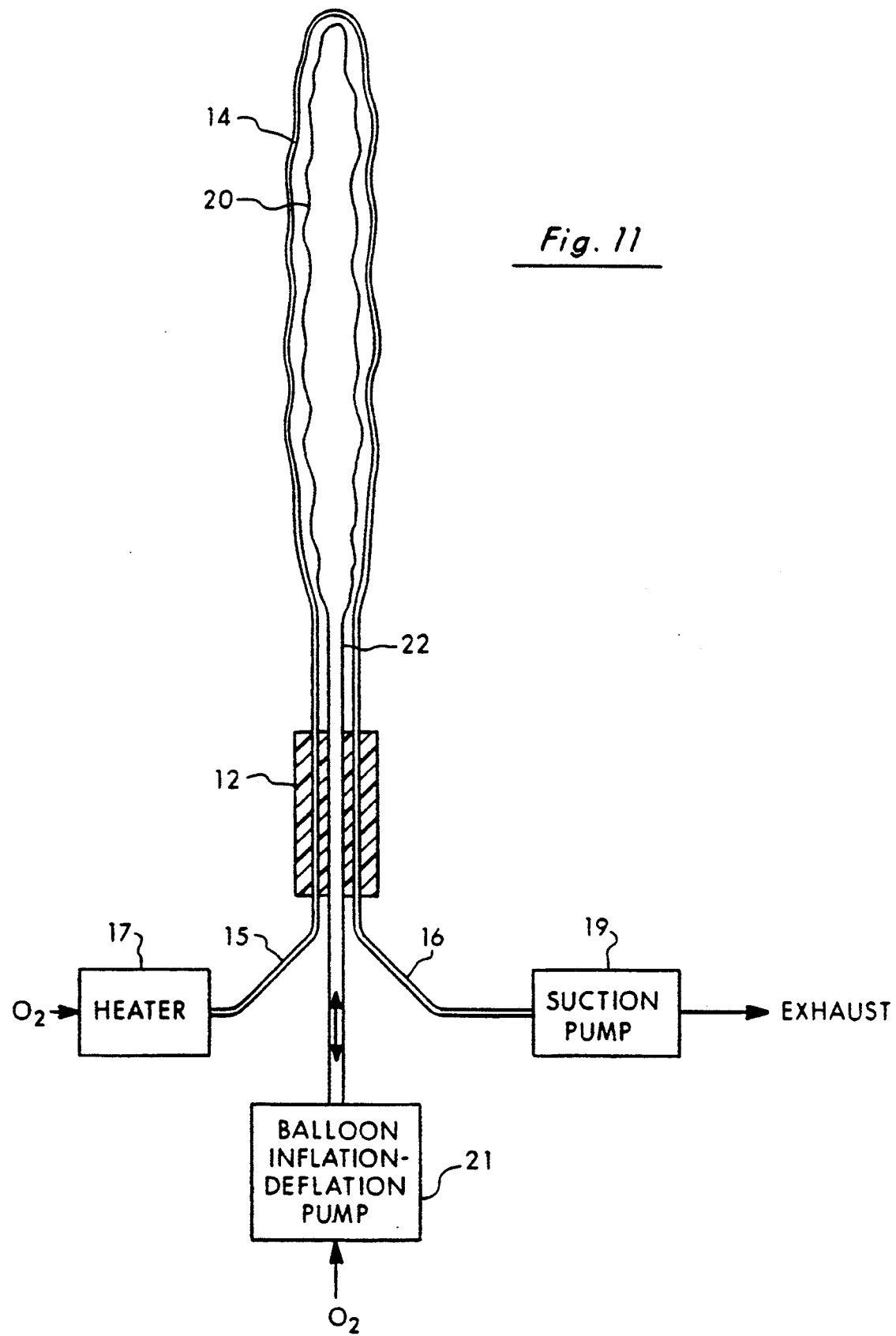
FIG. 11 is a side cross-sectional view of another alternative embodiment in which a balloon made of a gas-permeable polymer is inflated and deflated with oxygen.
Figure 14:
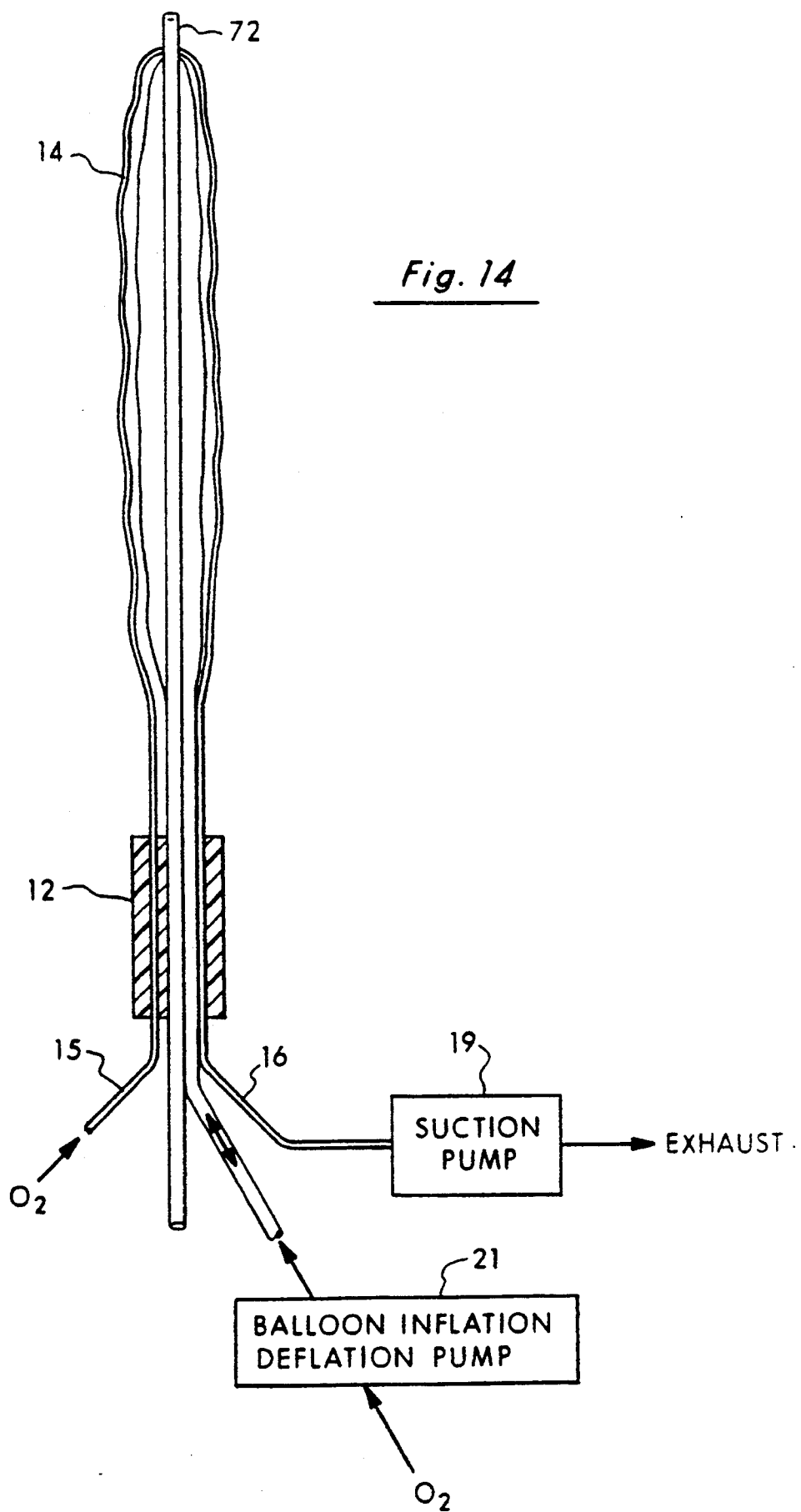
FIG. 14 is a side cross-sectional view of an alternative embodiment having a central guide wire to aid insertion of the device.

FIG. 11 is a cross-sectional view of another alternative embodiment wherein a balloon 20 made of a gas-permeable polymer is inflated and deflated with oxygen by the pump 21. The exchange of gases through the surface of the balloon 20 supplements the gas transfer between the bloodstream and the hollow gas-permeable fibers 14. The balloon is made of a synthetic polymer, such as gas-permeable polyethylene, polypropylene, or polyurethane. For example, in one embodiment, the balloon is inflated with oxygen at a flow rate of approximately 0.2 to 1.5 liters per minute and a pressure of approximately 10 to 100 mm Hg. The flow rate and pressure of the oxygen in the fibers would be the same as in the embodiment of FIGS. 1–5. FIG. 14 is a cross-sectional view of an alternative embodiment having a central guide wire 72 to aid insertion of the device.

Figure 12:
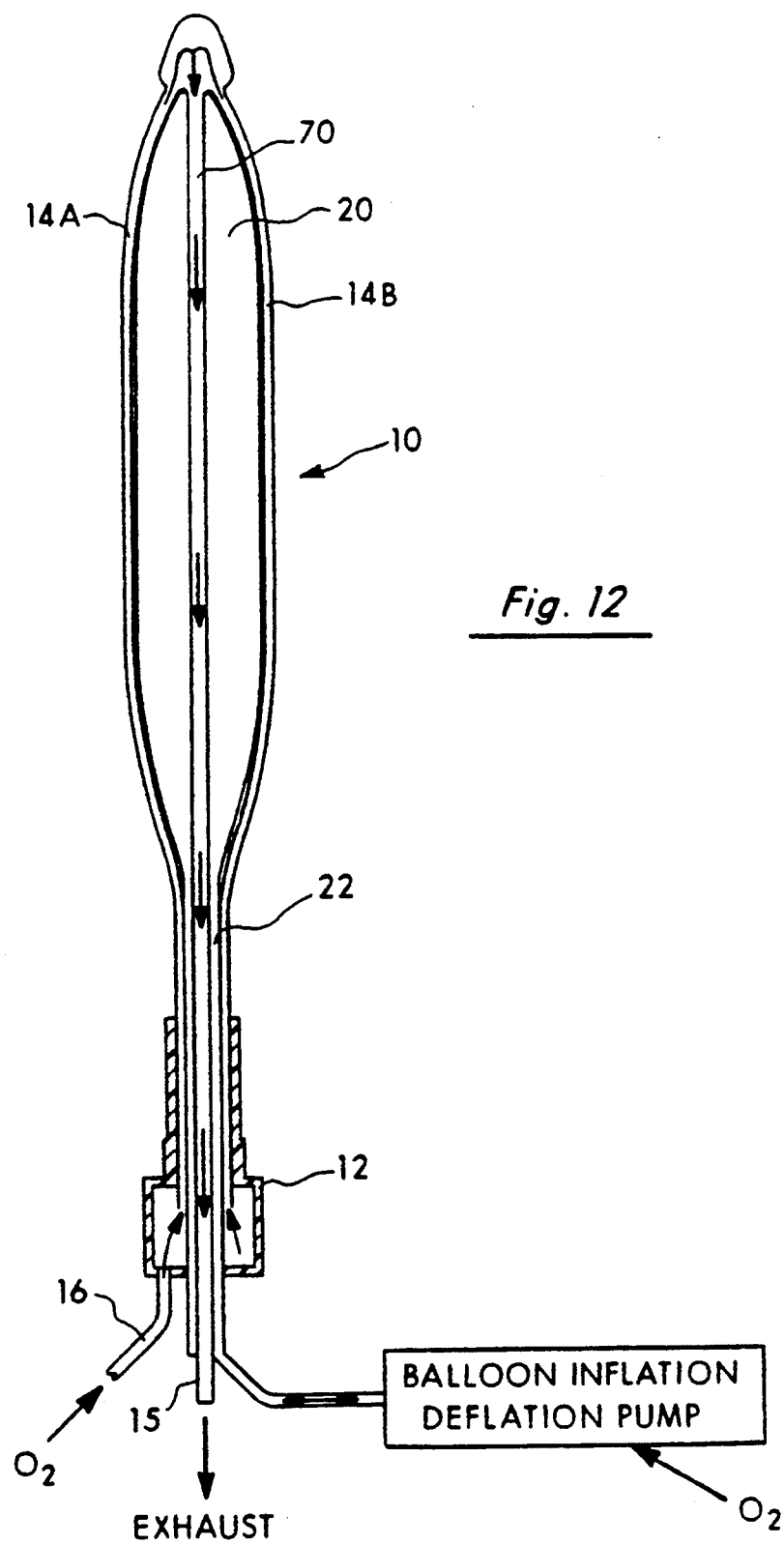
FIG. 12 is a side cross-sectional view of an alternative embodiment having a central oxygen supply tube, a hollow tip member, and a balloon made of a gas permeable polymer which is inflated and deflated with oxygen.

FIG. 12 is a cross-sectional view of another alternative embodiment similar to that shown in FIG. 11. Again, a balloon 20 made of a gas-permeable polymer is inflated and deflated with oxygen to supplement the gas transfer between the bloodstream and the hollow gas-permeable fibers 14a and 14b. A central oxygen exhaust tube 70 and a hollow tip member 100 exhaust oxygen from the fibers 14a and 14b, similar to the embodiment shown in FIG. 6.

Figure 13:
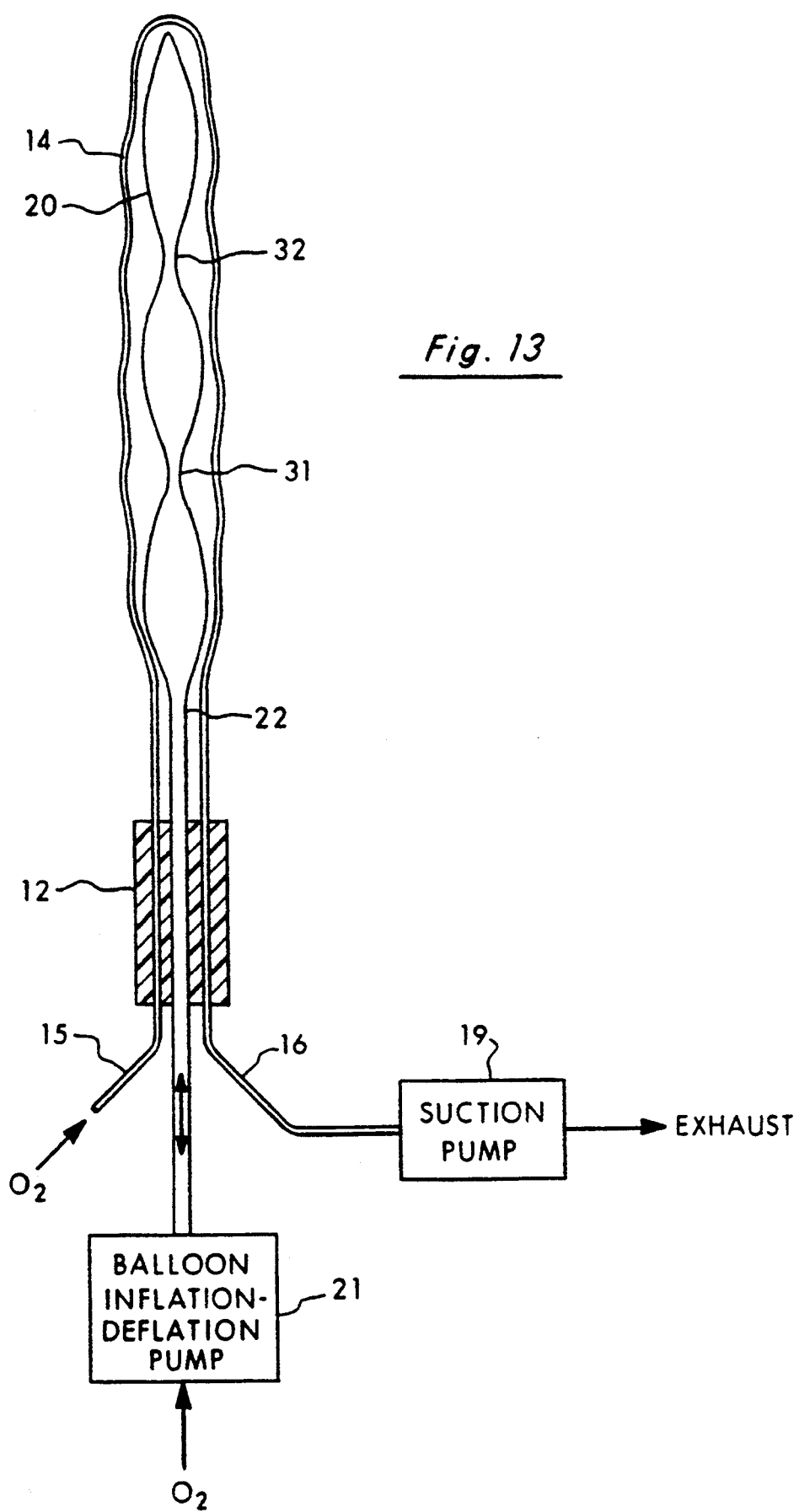
FIG. 13 is a side cross-sectional view of an alternative embodiment having a multi-chamber balloon in which the chambers are connected in series and are separated by constrictions to provide peristaltic motion to the balloon.
Figure 15:
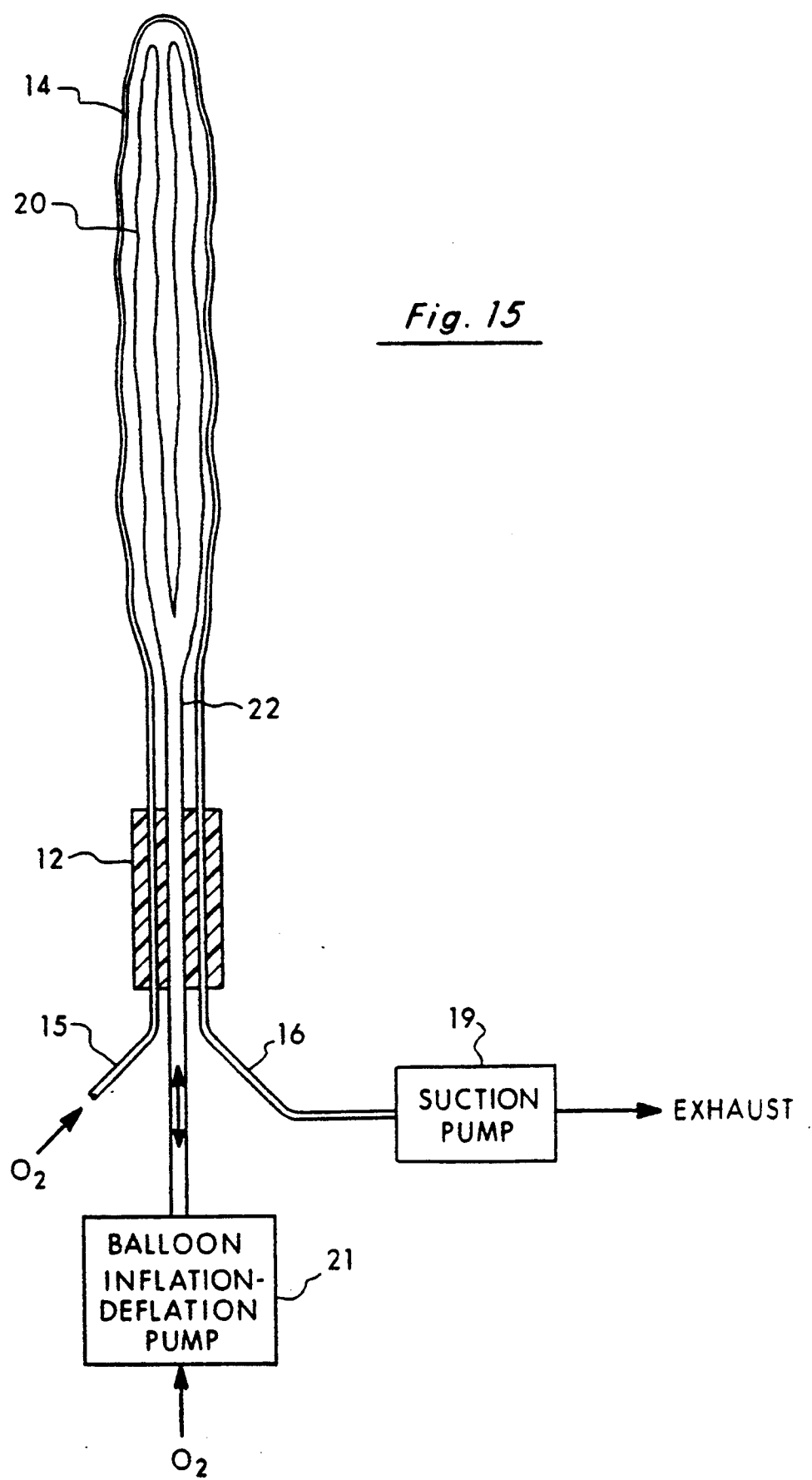
FIG. 15 is a side cross-sectional view of an alternative embodiment having a multi-chamber balloon in which the chambers are connected in parallel with one another.

FIG. 13 is a cross-sectional view of yet another embodiment having a multi-chamber balloon 20. The chambers of the balloon are connected in series separated by constrictions 31 and 32. The pump 21 repeatedly inflates and deflates the balloon 20 with oxygen at a predetermined frequency. The constrictions separating the balloon chambers restrict the flow of gases between the chambers, resulting in a relative phase shift in the inflation and deflation of the balloon chambers to provide peristaltic motion to the chambers of the balloon 20. In one embodiment, a constriction diameter of approximately 2 to 3 mm. has been found satisfactory. FIG. 15 is a cross-sectional view of an embodiment having a multi-chamber balloon 20 in which the balloon chambers constitute a plurality of longitudinally extending fingers. Operating parameters for delivery of oxygen would be the same as for the embodiment shown in FIGS. 1–5.

The cross-diffusion of gases from the hollow fibers 14 can be significantly enhanced by using the suction pump 19 to induce gentle pulsatile flow within the fibers 14. Pulsatile flow maximizes turbulent flow and mixing of the oxygen and carbon dioxide within the fibers to enhance cross-diffusion. For example, rates of 10 to 60 pulses per minute have been found satisfactory in one experimental embodiment.

Experimental testing has uncovered a potential problem of water condensation within the hollow fibers 14. Water droplets can block or obstruct the small passageways within the hollow fibers and thereby reduce the effective gas transfer rate between the fibers and the bloodstream. This condensation of water can occur when relative cool (e.g. room temperature) oxygen is fed into the fibers. The resulting temperature difference between the cool oxygen and patient's body temperature can be sufficient to cause water vapor entrained in the gases diffusing inwardly from the patient's bloodstream to condense inside the fibers. This problem can be avoided by warming the oxygen with a heater 17 to approximately body temperature (e.g. 34 to 37 degrees centigrade) before it is circulating through the fibers, as shown in FIG. 11.

A still further embodiment of the present invention is illustrated in FIGS. 16 through 18. The oxygenator in this embodiment includes an external connector 80 having an elongated substantially cylindrical neck 82 at one end and a bifurcated manifold 84 at the other end. A hollow passage through the neck provides a location for conventionally anchoring the proximal end of the fibers 14 so that they extend outwardly away from the connector 80 and terminate at a distal end in fluid communication with a hollow tip member 100. The balloon 20 is disposed in an area surrounded by the fibers and some of the fibers may be affixed to an external surface of the balloon. A semi-rigid, solid support rod 86 is secured at a distal end to the hollow tip 100 and protrudes completely through the external connector 80 at its other end so that the rod can serve to facilitate insertion of the device into the venous system and support the balloon and fibers within the venous system.

The bifurcated manifold system 80 circumscribes a central passage 87 through which the rod 86 extends and which also accommodates a tube 88 which is in fluid communication with the interior of the balloon 20 to facilitate inflation and deflation of the balloon. The bifurcated manifold defines two segregated semi-circular manifold sections 84i and 84e with section 84i being in fluid communication with one set 14i of approximately half of the fibers 14 at their proximal ends and the other section 14e in fluid communication with the a second set 14e of the fibers at their proximal ends. An oxygen inlet tube 90 is in communication with section 84i of the manifold while a gas exhaust tube 92 is in communication with the other manifold section 84e.

As with the embodiment shown in FIG. 1, appropriate pumps and vacuum sources are connected to the device for its operation.

The device is operated by supplying oxygen gas to section 84i of the manifold so that the gas flows into the first set of fibers 14i in communication therewith and flows outwardly through the fibers 14i and through the hollow tip 100 before being returned through the second set of fibers 14e to the exhaust section 84e of the manifold for removal from the device through the exhaust tube 92. The balloon is inflated and deflated in a manner described with previously described embodiments through the tube 88 associated therewith.

Figure 19:
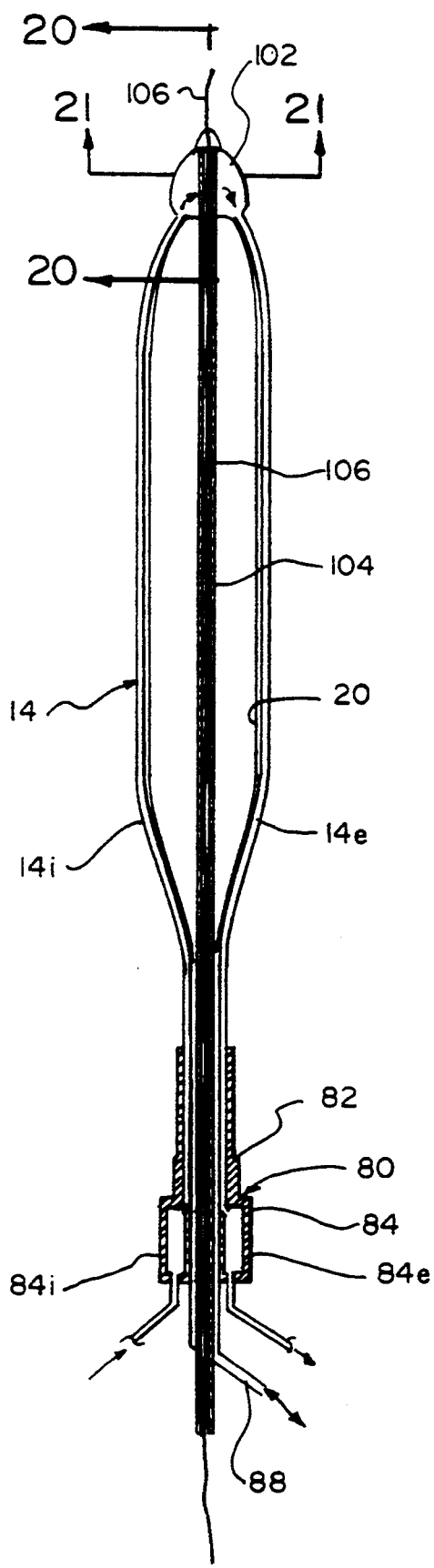
FIG. 19 is a cross-sectional view of still a further embodiment wherein a hollow tube is utilized to support the balloon and fibers as well as to facilitate sliding movement of the oxygenator along a guide wire.
Figure 20:
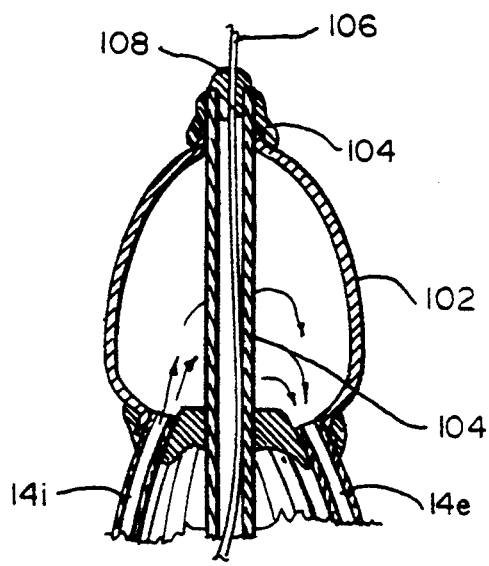
FIG. 20 is an enlarged section taken along line 20—20 of FIG. 19.
Figure 21:
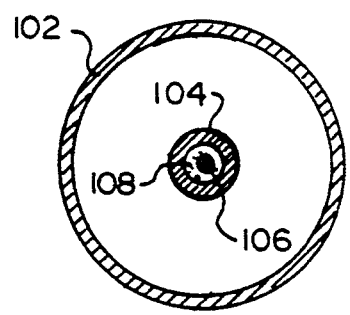
FIG. 21 is an enlarged section taken along line 21—21 of FIG. 19.

A further embodiment of the invention is shown in FIGS. 19 through 21 to be very similar to the embodiment shown in FIGS. 16 through 18 so as to have an external connector 80 with a neck 82 and a bifurcated manifold 84 such that each section of the manifold 84$i$ and 84$e$ is associated with set 14$i$ or a set 14$e$ respectively of the fibers 14 so that oxygen gas can be delivered to section 84$i$ of the manifold and exhaust gas removed from section 84$e$ after the gas is passed outwardly through the first set of fibers 14$i$ associated with the inlet manifold, passed through a hollow tip 102 and returned through the second set of fibers 14$e$ associated with the exhaust manifold 84$e$. The balloon 20, of course, is again disposed in an area surrounded by the fibers and some of the fibers may be affixed to an external surface of the balloon. A gas delivery and removal tube 88 is connected thereto. A support rod 104 in this embodiment is hollow and protrudes not only through the connector 80 and the interior of the balloon 20 but also hermetically through the hollow tip 102 and through a hollow cap 104 provided on the distal end of the hollow tip 102. A guide wire 106 can be passed through the hollow support rod 104 and through a sealing plug 108 in the cap 104.

As with the embodiment shown in FIGS. 16–18, appropriate pumps and vacuum sources are connected to the device for its operation.

The operation of this embodiment of the invention for oxygenation purposes is identical to that of the embodiment shown in FIGS. 16 through 18, but the device is inserted into the venous system by first feeding the guide wire 106 through the hollow support rod 104 and then inserting the guide wire into the venous system to the point where it is desirable to position the oxygenator. After the guide wire is so positioned, the oxygenator can be advanced or slid along the guide wire to the desired location in a simple and efficient manner.

The above disclosure sets forth a number of embodiments of the present invention. Other arrangements or embodiments, nor precisely set forth, could be practiced under the teachings of the present invention and as set forth in the following claims.

I claim:

1. An inflatable percutaneous oxygenator adapted to extend through a single incision in a patient into a blood vessel, said oxygenator comprising:
   an inflatable balloon for at least partial insertion into said blood vessel having an exterior surface permitting selective expansion and contraction of said balloon by introducing gas into and removing gas from said balloon respectively,
   an external connector for insertion through said incision into the patient adjacent to said balloon having a first lumen to permit inflation and deflation of said balloon, a second lumen to deliver a supply of oxygen-containing gas to said oxygenator and a third lumen to exhaust gas from said oxygenator,
   pump means connected to said first lumen of said connector to alternately expand and contract said balloon,
   a first group of hollow, gas-permeable fibers, each fiber of said first group having a first end operatively connected to said external connector in fluid communication with said second lumen, and a second end,
   a hollow tip member removed from said external connector having an internal cavity, said second end of said first group of fibers being operatively connected to said tip member in fluid communication with said internal cavity, and
   a second group of hollow, gas-permeable fibers, each fiber in said second group having a first end operatively connected to said tip member in fluid communication with said internal cavity and a second end operatively connected to said external connector in fluid communication with said third lumen, said first and second group of fibers substantially surrounding at least a portion of said balloon.

2. The oxygenator of claim 1 wherein said pump means repeatedly inflates and deflates said balloon at a predetermined frequency.

3. The oxygenator of claim 1 further comprising an elongated support member extending from said external connector to support said fibers with respect to said connector.

4. The oxygenator of claim 1 wherein at least a portion of said fibers are secured to the exterior surface of said balloon.

5. The oxygenator of claim 1 further comprising suction means operatively connected to said third lumen adapted to exhaust gas from said second group of fibers at a negative pressure.

6. The oxygenator of claim 3 wherein said support member is a solid rod.

7. The oxygenator of claim 3 wherein said support member is a hollow rod.

8. The oxygenator of claim 7 further including a guide wire slidably extending through said support member such that the guide wire can be advanced into said blood vessel and serve as a guide for inserting the hollow fibers into the blood vessel by sliding the support member along the guide wire.

9. The oxygenator of claim 1 wherein said external connector further includes an inlet manifold in fluid communication with said second lumen and the first end of said first group of fibers and an exhaust manifold in fluid communication with said third lumen and the second end of said second group of fibers.

* * * * *

UNITED STATES PATENT AND TRADEMARK OFFICE
CERTIFICATE OF CORRECTION

PATENT NO. : 5,376,069

DATED : December 27, 1994

INVENTOR(S) : Brack G. Hattler; of Pittsburgh, Pennsylvania

It is certified that error appears in the above-indentified patent and that said Letters Patent is hereby corrected as shown below:

Column 1, Line 47              "--tort--" should read -- torr --

Signed and Sealed this

Fourth Day of July, 1995

Attest:

BRUCE LEHMAN

Attesting Officer       Commissioner of Patents and Trademarks